United States Patent
Komiya

[11] 3,958,576
[45] May 25, 1976

[54] SURGICAL INSTRUMENT FOR CLIPPING ANY AFFECTED PORTION OF A BODY CAVITY

[75] Inventor: Osamu Komiya, Hachioji, Japan

[73] Assignee: Olympus Optical Co., Ltd., Tokyo, Japan

[22] Filed: Nov. 12, 1974

[21] Appl. No.: 523,071

[30] Foreign Application Priority Data
Nov. 14, 1973 Japan.................. 48-130727[U]

[52] U.S. Cl. ................... 128/346; 24/260; 29/243.56; 30/187
[51] Int. Cl.² ............... A61B 17/08; A61B 17/10
[58] Field of Search................. 29/225, 229, 243.56; 24/260, 261 C; 30/179, 175, 187; 128/325, 346

[56] References Cited
UNITED STATES PATENTS

| | | | |
|---|---|---|---|
| 450,266 | 4/1891 | Truax.................... | 128/346 |
| 809,551 | 1/1906 | Brunner................. | 24/260 UX |
| 3,310,872 | 3/1967 | Dowdell................ | 30/187 |

Primary Examiner—Channing L. Pace

[57] ABSTRACT

A clip member of substantially a figure "eight" shape is detachably attached to an instrument body. The instrument body has an outer flexible tube, an actuating tubular member inserted into the outer tube, and a wire inserted into the actuating tubular member. A holder is detachably mounted through a guide member to the forward end portion of the actuating member. To the forward end of the wire is secured a hook member for anchoring the clip member. A pair of clamping portions of the clip member is opened by forcefully engaging a pair of offset portions of the clip member with the inner surface of the holder, and closed by forcefully engaging a pair of intersecting portions with the inner surface of the holder. As a result, any affected portion of a body cavity of a human being is clipped by the clip member associated with the holder. The clip member, together with the holder, is left within the body cavity with the clamping portions thereof closed.

12 Claims, 7 Drawing Figures

SURGICAL INSTRUMENT FOR CLIPPING ANY AFFECTED PORTION OF A BODY CAVITY

BACKGROUND OF THE INVENTION

This invention relates to a surgical instrument for clipping any affected portion of a body cavity of a human being.

The resection of any affected portion of a body cavity is conventionally effected for medical purposes by inserting forceps into the body cavity of a human being through manupulation of an endoscope etc. The electrical searing or cauterization of any diseased portion of a body cavity is also conducted by inserting an electrical surgical instrument into the body cavity.

According to the conventional method a greater amount of blood is oozed from the injured portion of the body cavity in cutting out the affected portion of the body cavity. Furthermore, it is difficult to cure the injured portion of the body cavity. There is also a fear that during the movement of the forceps within the body cavity the forceps is contacted with a portion other than the affected portion of the body cavity to cause injury thereto.

Recently, there has been developed a new method according to which a tubular surgical instrument with a clip member attached at its forward end portion is inserted through an endoscope into the body cavity of a human being and any affected portion of the body cavity is clipped by the clip member. The clip member is left within the body cavity until the clipped portion of the body cavity is necrosed and dropped, together with the clip member, down onto the inner wall of the body cavity. The dropped necrosed portion is excreted, together with the clip member, from the system. In this method the above-mentioned drawbacks can be eliminated.

The clip member now in use is made of, for example, a substantially V-shaped leaf spring and has a pair of clamping portions urged in a direction in which they are closed. The surgical instrument with a clip member attached at its forward and portion is inserted through the endoscope into the body cavity of a human being. The clamping portions of the clip member are opened against a spring biasing force to permit any diseased portion of the body cavity to be captured therebetween. Upon releasing the spring urging force, the clip member is closed under its own urging force to cause the diseased portion of the body cavity to be clipped. With the clip member so constructed, however, the clamping portions cannot provide a greater opening angle therebetween. If the clamping portions of the clip member are opened to a too great extent, there is a fear that they will not be returned to an original closed position. It is therefore impossible to clip any greater diseased portion of the body cavity. Furthermore it is difficult to capture any smaller diseased portion of the body cavity between the clamping portion of the clip member.

SUMMARY OF THE INVENTION

It is accordingly the object of this invention to provide a surgical instrument for clipping any diseased portion of a body cavity of a human being, which is capable of providing a greater opening angle between the clamping portions of a clip member and capable of easily opening and closing the clip member without fail.

The features of this invention reside in that the surgical instrument has a clip member of substantially a figure "eight" shape; the clip member is attached through a hook member to the forward end portion of the instrument body; the clip member is opened and closed by shifting a position in which engaging means is engaged with the clip member; the engaging means serves to keep the clip member in a closed position in an attempt to clip any diseased portion of the body cavity; and the clip member is left, together with the engaging means, within the body cavity of a human being.

Since, according to this invention, a greater opening angle can be provided between the clamping portions of the clip member, it is possible to clip a greater diseased portion of the body cavity. Furthermore, it is easy to capture any diseased portion of the body cavity. A positive clipping is also assured, as the engaging means are forcefully engaged with the clip member.

DESCRIPTION OF THE PREFERRED EMBODIMENTS

Figure 1:
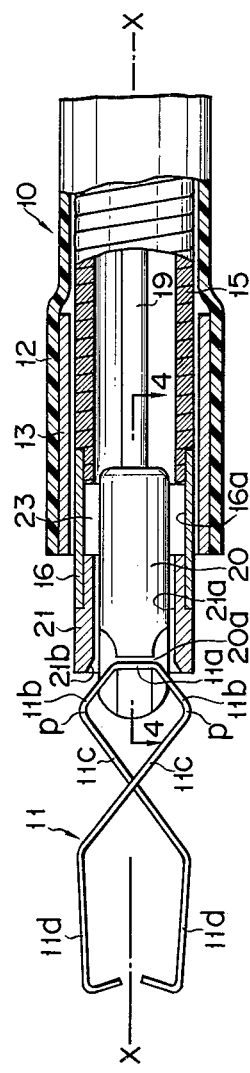
FIG. 1 is a partial side view, partly broken away, showing a surgical instrument according to this invention.

In FIG. 1 a clip member 11 is attached at the forward end of a body 10 of a surgical instrument according to this invention. The clip member 11 is attached as shown in FIG. 1 at the forward end of the body 10 of the surgical instrument before the surgical instrument is inserted through an endoscope, not shown, into the body cavity of a patient.

The clip member is formed by bending an elongated metal sheet into a shape of a figure "eight" as shown in FIG. 1, and comprises a rear end portion 11a, a pair of offset portions 11b having one end connected to the rear end portion 11a and the other end outwardly extending away from an axis X—X thereof, a pair of portions 11c connected to the other end of the offset portions 11b and intersecting each other, and a pair of clamping portions 11d connected to the other end of the intersecting portions 11c.

Figure 3:
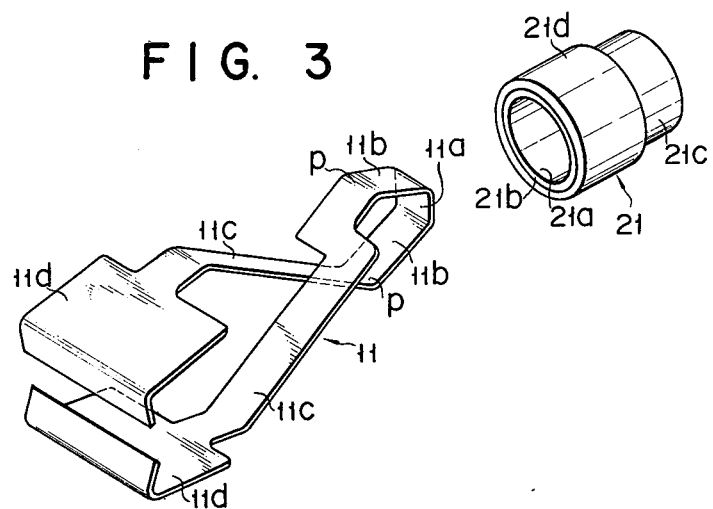
FIG. 3 is a perspective view showing a clip member and a holder.
Figure 6:
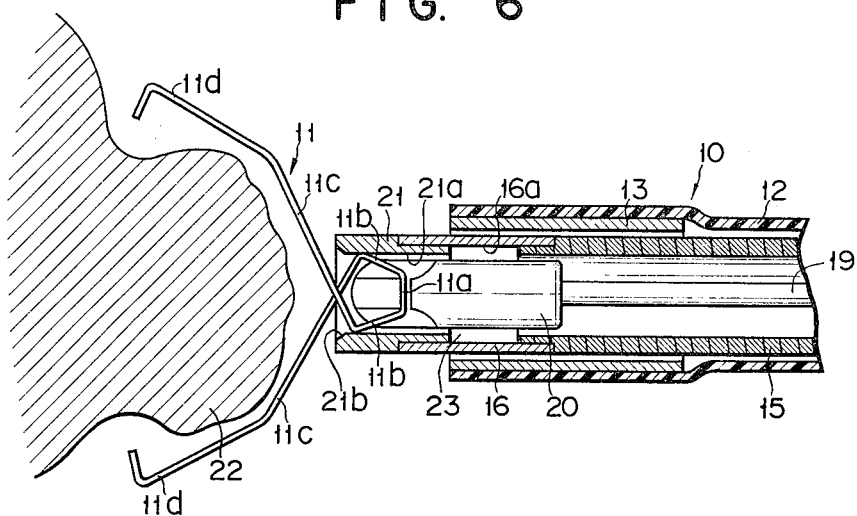
FIG. 6 is an explanatory view showing the manner in which any diseased portion of a body cavity of a human being is captured by the clip member.
Figure 7:
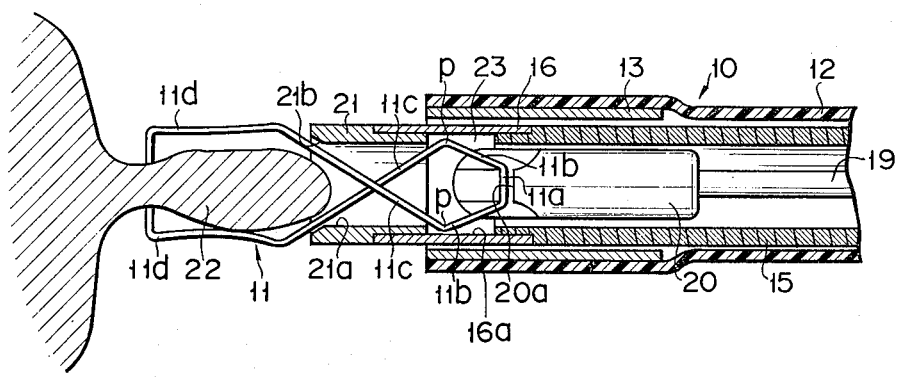
FIG. 7 is an explanatory view showing the manner in which any diseased portion of the body cavity of a human being is clipped by the clip member.

As shown in FIG. 3 the nipping portion 11d of the clip member 11 is made fairly wider than the offset portion 11b and intersecting portion 11c thereof. Clamping portions 11d are opened and closed as shown in FIGS. 6 and 7 by engagement with a holder 21.

Figure 2:
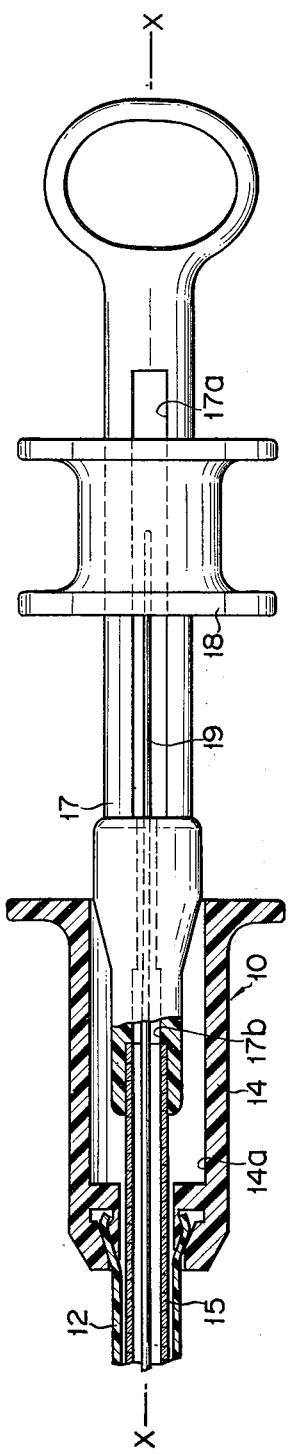
FIG. 2 is a partial side view showing the base portion of a surgical body.

The body 10 of the surgical instrument has a lengthy outer flexible tube 12 made of synthetic resin. As shown in FIG. 2, the outer flexible tube 12 extends from the forward end toward the base of the instrument body. Into the forward end portion of the outer flexible tube 12 is fitted a cylindrical reinforced metal member 13 for retaining the tubular shape of the outer flexible tube 12. The base end portion of the outer tube 12 is attached to a holding member 14 made of synthetic resin.

A tubular actuating member 15 is slidably inserted into the outer flexible tube 12 along the length of the outer flexible tube 12. The actuating member 15 is formed by compactly winding a fine metal wire in a coil spring-like fashion. A thin-walled cylindrical metal guide member 16 having a hole 16a opened at both ends thereof is connected to the forward end of the actuating member 15 as shown in FIG. 1. The base portion of the actuating member 15 is fitted, as shown in FIG. 2, into an operating member 17 made of synthetic resin. The portion of the operating member 17 is received within a hole 14a formed in the holding member 14. When the operating member 17 is moved relative to the holding member 14, the actuating member 15 is slidably and axially moved relative to the outer tube 12. An elongated axial groove 17a is formed substantially at the middle of the operating member 17. A sliding member 18 is so fitted over the operating member 17 as to be slidably movable along the elongated groove 17a in the axial direction of the operating member.

A lengthy metal wire 19 is inserted within and over the length of the actuating member 15. As shown in FIG. 1 the wire 19 is connected at its free end to a hook member 20 and at its base end to the sliding member 18 through an axial hole 17b formed in the operating member 17. When the sliding member 18 is slidably moved relative to the operating member 17 the wire 19 is moved within the actuating member 15 and, in consequence, the hook member 20 is axially moved within the forward end portion of the actuating member 15.

Figure 4:
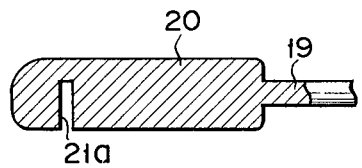
FIG. 4 is a cross sectional view taken along line 4—4 of FIG. 1.

The hook member 20 has a cutout 20a at its side. The cutout 20a is formed, as shown more clearly in FIG. 4, perpendicular to the axis of the hook member 20. Within the cutout 20a of the hook member 20 the rear end portion 11a of the clip member 11 is detachably anchored.

A cylindrical holder 21 constituting an engaging means is stepped in its outer diameter and has a large diameter portion 21d and a small diameter portion 21c. The holder 21 is opened at both the ends thereof and has an engaging hole 21a. The forward end portion of the guide member 16 is detachably fitted over the small diameter portion 21c of the holder 21.

The operation of the surgical instrument according to this invention will now be described.

The holder 21 is inserted into the guide member 16 and the rear end portion 11a of the clip member 11 is anchored in the cutout 20a of the hook member 20 as shown in FIG. 1 before the surgical instrument is inserted into the body cavity of a patient.

On attaching the holder 21 and clip member 11 to the instrument body 10 the operating member 17 is forced into the holding member 14 so that the hook member 20 can project from the forward end of the outer tube 12. During the forcing of the operating member 17 into the holding member 14 the sliding member 18 is also moved forwardly to its extreme extent.

Figure 5:
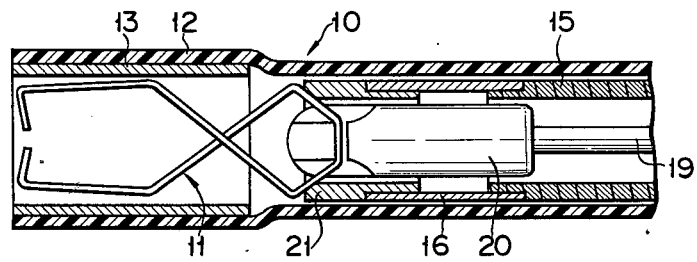
FIG. 5 is a partial side view showing a position in which a clip member is received within the instrument body.

After the holder 21 and clip member 11 is attached, as shown in FIG. 1, to the instrument body 10 the operating member 17 is withdrawn from the holding member 14 and thus the sliding member 18 is withdrawn. The withdrawal of the operating member 17 and sliding member 18 permits the clip member 11 and holder 21 to be completely received within the outer flexible tube 12 as shown in FIG. 5. If, at this time, the sliding member 17 is slightly moved backward relative to the operating member 17 so as to permit the hook member 20 to be slightly moved backward, a taper surface 21b formed at the inner surface of the forward end of the holder 21 is lightly contacted as shown in FIG. 5 with the pair of offset portions 11b of the clip member 11, thereby preventing the clip member 11 from dropping away from the hook member 20.

After the holder 21 and clip member 11 are so received within the outer flexible tube 12, the surgical instrument is inserted, for example, throught an endoscope, not shown, into the body cavity of the patient. When any affected portion 22 to be clipped—for example, polyp etc.—is discovered during the observation of the body cavity, the forward end of the surgical instrument is brought up to the portion 22 of the body cavity by manupulating the endoscope. Since, during this process, the clip member 11 is received completely within the outer flexible tube 12, even if the forward end of the instrument is abutted against the inner wall of the body cavity, no injury is made to the inner wall of the body cavity.

After the forward end of the surgical instrument is brought into face to face with the affected portion 22, such as polyp etc., of the body cavity, the operating member 17 and sliding member 18 are moved forward, as a unit, relative to the holding member 14 to cause the hook member 20 and holder 21 to be exposed from the outer tube 12. Then, the sliding member 18 and thus the wire 19 are slightly withdrawn relative to the operating member 17 to permit only the hook member 20 to be retracted relative to the holder 21. Since the inner diameter of the engaging hole 21a of the holder 21 is smaller than a distance between the junctions p of the offset portions 11b and intersecting portions 11c of the clip member 11, the offset portions 11b of the clip member 11 are abutted, during the withdrawal of the hook member 20, against the tapered portion 21b of the holder 21 and further withdrawn, as shown in FIG. 6, into the engaging hole 21 to cause the offset portions 11b of the clip member 11 to be compressed to permit the pair of clamping portions 11d of the clip member 11 to be greatly opened. During this process, an intersecting angle made between the intersecting portions 11c of the clip member 11 is varied and the position of an intersection made between the intersecting portions 11c of the clip member 11 is shifted. The portion 22 of the body cavity is captured as shown in FIG. 6 between the clamping portions 11d of the clip member 11.

Thereafter, the sliding member 18 and thus the wire 19 are further withdrawn relative to the operating member 17 to cause the hook member 20 to be retracted as shown in FIG. 7. In the position shown, the holder 21 is disengaged from the offset portions 11b of the clip member 11 and engaged with the intersecting poritons 11c of the clip member 11 to cause the clamping portions 11d of the clip member 11 to be closed to permit the neck of the portion 22 of the body cavity to be clipped. During this process, said intersecting angle of the clip member 11 is varied and the position of said intersection of the clip member 11 is shifted.

When the hook member 20 is retracted, as shown in FIG. 7, within the forward end portion of the outer flexible tube 12, the offset portions 11b of the clip member 11 is positioned within the hole 16a of the guide member 16 and between the forward end of the actuating member 15 and the rear end of the holder 21. Since, however, the hole 16a of the guide member 16 is large enough to allow a clearance to be formed with respect to the junctions p between the offset portions 11b and intersecting portions of the clip member 11c, the offset portions 11b of the clip member 11 are not urgingly compressed by the guide member 16. Within the guide member 16 is formed a space 23 defined by the rear end of the holder 21 and the forward end of the actuating member 15.

After the clip member 11 so clips the affected portion 22 of the body cavity, the sliding member 18 and thus the wire 19 are pushed forward relative to the operating member 17 to cause the hook member 20 to be advanced together with the clip member 11. At this time, the holder 21 trapped at the intersecting portions 11c of the clip member 21 is moved out of engagement with the guide member 16 and pushed forward together with the clip member 11. If after the complete exposure of the clip member 11 the forward end portion of the surgical instrument is moved sidewise, by manipulating the endoscope, the rear end portion 11a of the clip member 11 is disengaged from the cutout 21a of the hook member 20. Consequently, the clip member 11 and holder 21 are removed completely from the instrument body 10 and left within the body cavity. In other words, the portion 22 of the body cavity is left clipped by the clip member 11 associated with the holder 21.

The holder 21 serves to maintain the clipping engagement of the clip member 11 with the affected portion 22 of the body cavity and the clamping portions 11d of the clip member 11 is maintained in a closed position. Therefore, there is no fear that the clip member 11 will inadvertently drop away from the affected portion 22 of the body cavity.

Since, as mentioned above, the clamping portions 11d of the clip member 11 can be opened wide by engaging the offset portions in b of the clip member 11 with the inner surface of the holder 21, a greater affected portion of the body cavity can be clipped between the clamping portions 11d of the clip member 11. Furthermore, the affected portion of the body cavity can be more easily and assuredly captured, as the clamping portions 11d of the clip member 11 is made relatively wide. The clip member 11 can be easily attached and detached to and from the instrument body and the clamping portions 11d of the clip member 11 can be easily opened and closed without fail.

What is claimed is:

1. A surgical instrument for clipping any affected portion of a body cavity of a human being, comprising a clip member formed into a substantially figure "eight" shape and having a rear end portion, a pair of offset portions having one end connected to the rear end portion and the other end extending away from the longitudinal axis of the clip member, a pair of portions respectively connected at one end to the opposite ends of the offset portions and intersecting each other, and a pair of clamping portions respectively connected to the opposite ends of the intersecting portions; an instrument body through an interior of which the clip member is introduced into the body cavity; a hook member mounted within the instrument body so as to anchor the rear end portion of the clip member; first actuating member for moving the hook member anywhere between a first position in which the hook member is exposed and a second position in which the hook member is retracted within the instrument body; engaging means adapted to be forcefully engaged with the offset portions of the clip member, when the hook member is retracted a predetermined distance from the first position, to cause the offset portions to be urgingly compressed to move the clamping portions of the clip member to an opened position, adapted to be forcefully engaged with the intersecting portions of the clip member, when the hook member is further retracted by the first actuating means, to cause the clamping portions of the clip member to be closed to clip the affected portion of the body cavity, and adapted to be left, together with the clip member within the body cavity when the clip member associated therewith is separated from the instrument body; and second actuating means for moving the engaging means relative to the hook member anywhere between a first position in which the engaging means is exposed and a position in which the engaging means is retracted.

2. A surgical instrument according to claim 1, in which said clip member is made of a sheet of metal.

3. A surgical instrument according to claim 1, in which the clamping portion of the clip member is wider than the offset portion and intersecting portion of the clip member.

4. A surgical instrument according to claim 1, in which said clip member is anchored by the hook member and, when retracted to its extreme extent, is received within the instrument body.

5. A surgical instrument according to claim 1, in which said first actuating means includes a lengthy wire movable within the instrument body and having a free end connected to the hook member.

6. A surgical instrument according to claim 1, in which said engaging means is a cylindrical member opened at both the ends thereof.

7. A surgical instrument according to claim 6, in which said second actuating means comprises a lengthy tubular actuating member movable within the instrument body and thin-walled cylindrical guide member opened at both the ends thereof, said cylindrical member being slidably fitted into the forward end portion of the guide member.

8. A surgical instrument according to claim 7, in which said cylindrical member is stepped in its outer diameter and has a front large diameter portion and a rear small diameter portion, and the small diameter portion is fitted into the forward end portion of the guide member.

9. A surgical instrument according to claim 8, in which, when the intersecting portions of the clip member are urgingly engaged with the cylindrical member by withdrawing the hook member by virtue of the first actuating means, the offset portion of the clip member are positioned within an inner hole of the guide member and between the forward end of the diameter of the inner hole of the guide member is large enough to allow a clearance to be formed with respect to a junction between the offset portion and intersecting portion of the clip member.

10. A surgical instrument according to claim 4, in which said hook member has a cutout formed at the side surface thereof and in a direction substantially perpendicular to the axis thereof and the rear end portion of the clip member is anchored in the cutout of the hook member.

11. A surgical instrument according to claim 1, in which said instrument body includes a flexible outer tube adapted to be inserted into an endoscope.

12. A surgical instrument according to claim 1, in which said instrument body includes a lengthy outer flexible tube and a rigid cylindrical member connected to the forward end of the outer flexible tube; said second actuating means includes a lengthy tubular actuating member inserted into the outer flexible tube; said first actuating means includes a lengthy wire slidably inserted therein and having a free end connected to the hook member; and said hook member has a cutout for anchoring the clip member.

* * * * *